(12) United States Patent
Tjiong et al.

(10) Patent No.: US 6,900,316 B2
(45) Date of Patent: May 31, 2005

(54) PROCESS FOR PREPARING 2-(4-PYRIDYL) AMINO-6-DIALKYLOXYPHENYL-PYRIDO(2, 3-D)PYRIMIDIN-7-ONES

(75) Inventors: Howard Isaac Tjiong, Holland, MI (US); Roy Thomas Winters, Pinckney, MI (US)

(73) Assignee: Warner-Lamber Company, Morris Plains, NJ (US)

( * ) Notice: Subject to any disclaimer, the term of this patent is extended or adjusted under 35 U.S.C. 154(b) by 6 days.

(21) Appl. No.: 10/343,803

(22) PCT Filed: Jul. 12, 2001

(86) PCT No.: PCT/US01/51422
§ 371 (c)(1),
(2), (4) Date: Feb. 4, 2003

(87) PCT Pub. No.: WO03/027110
PCT Pub. Date: Apr. 3, 2003

(65) Prior Publication Data
US 2003/0176700 A1 Sep. 18, 2003

Related U.S. Application Data
(60) Provisional application No. 60/222,866, filed on Aug. 4, 2000.

(51) Int. Cl.[7] ..................... C07D 471/04; C07D 239/47
(52) U.S. Cl. ........................ 544/279; 544/317
(58) Field of Search ......................... 540/279

(56) References Cited

U.S. PATENT DOCUMENTS

| | | | |
|---|---|---|---|
| 5,733,914 A | 3/1998 | Blankley et al. | |
| 5,945,422 A | 8/1999 | Doherty et al. | |
| 2003/0149001 A1 * | 8/2003 | Barvian et al. | 514/80 |
| 2003/0216415 A1 * | 11/2003 | Beylin et al. | 514/264.11 |
| 2003/0220345 A1 * | 11/2003 | Hamby et al. | 514/252.16 |

FOREIGN PATENT DOCUMENTS

| | | |
|---|---|---|
| WO | WO 96/34867 A1 | 11/1996 |
| WO | WO 01/44258 A1 | 6/2001 |

OTHER PUBLICATIONS

Andrew M. Thompson, et al., "Tyrosine kinase inhibitors. 7.7–amino–4–(phenylamino)– and 7–amino–4–[(phenylmethyl)amino]pyrido[4,3–d]pyrimidines: a new class of inhibitors of the tyrosine kinase activity of the epidermal growth factor receptor" J. Med. Chem, 1995, pp 3780—3788, vol. 38, No 19.

S. R. Klutchko, et al., "2–Substituted Aminopyrido[2,3–d] pyrimidin–7(8H)–ones. Structure Activity Relationships Against Selected Tyrosine Kinases and in Vitro and in Vivo Anticancer Activity", J. Med. Chem., 1998, pp 3276–3292, vol. 41.

D. H. Boschelli, et al., "Synthesis and Tyrosine Kinase Inhibitory Activity of a Series of 2–Amino–8H–pyrido[2, 3–d]pyrimidines: Identification of Potent, Selcetive Platelet–Derived Growth Factor Receptor Tyrosine Kinase Inhibitors" J. Med. Chem, 1998, pp 4365–4377, vol. 41.

* cited by examiner

Primary Examiner—Mark L. Berch
(74) Attorney, Agent, or Firm—Peter C. Richardson; Bryan C. Zielinski

(57) ABSTRACT

A process for preparing a 2-(pyridin-4-ylamino)-pyrido[2, 3-d]pyrimidine of Formula II

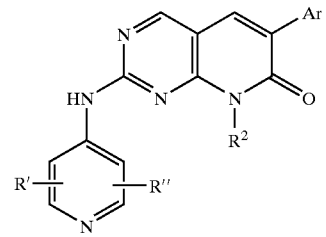

comprising reacting a 4-aminopyridine of the formula

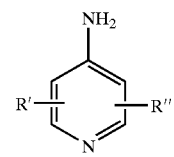

with an alkali metal amide or hydride and a 2-alkylsulfanyl-pyrido[2,3-d]pyrimidine of Formula I

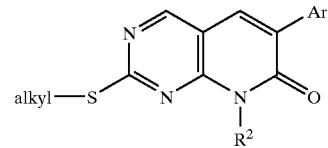

wherein $R^1$, $R^2$, R' and R", and aryl are as defined in the specification.

6 Claims, No Drawings

PROCESS FOR PREPARING 2-(4-PYRIDYL) AMINO-6-DIALKYLOXYPHENYL-PYRIDO(2,3-D)PYRIMIDIN-7-ONES

This application is a 371 application of PCT/US01/51422 filed Jul. 12, 2001, which claims the benefit of priority to U.S. provisional application Ser. No. 60/222,866 filed Aug. 4, 2000.

FIELD OF THE INVENTION

This invention concerns a chemical process for preparing pyrido[2,3-d]pyrimidines having a pyridylamino group at the 2-position.

BACKGROUND OF THE INVENTION

U.S. Pat. No. 5,733,914 (which is incorporated herein by reference) describes a series of pyrido[2,3-d]pyrimidines that inhibit protein tyrosine kinase mediated cellular proliferation. The compounds are anti-angiogenic agents, and as such are useful for treating cancer, particularly leukemia and breast cancer. The U.S. Pat. No. 5,733,914 patent teaches that a particularly preferred group of compounds are substituted at the 2-position with an arylamino group, and that the aryl moiety can be a pyridyl group. 2-(4-Pyridyl)amino-pyrido[2,3-d]pyrimidines appear to be a preferred group of compounds because of their metabolic stability and tyrosine kinase selectivity. One such compound, namely 2-(pyridin-4-ylamino)-6-(3,5-dimethoxyphenyl)-8-ethyl-8H-pyrido[2,3-d]pyrimidin-7-one, is currently being studied as a possible clinical candidate for treating cancer.

According to the synthetic process described in U.S. Pat. No. 5,733,914, an alkylsulfanyl (a sulfide) group could not be readily displaced by an amine such as a 4-aminopyridine, whereas an alkylsulfinyl group (a sulfoxide) could be so displaced. Accordingly, the 2-alkylsulfanyl pyridopyrimidines first had to be oxidized to provide the corresponding sulfoxide, namely a 2-alkylsulfinyl pyridopyrimidine. The use of such oxidants is not only dangerous on large scale and often causes over-oxidation, but also is very costly, given that the oxidants are expensive and the process adds another chemical step and isolation. This invention avoids these expenses.

Because these compounds are commercially viable anticancer agents, the need exists for a synthetic process that affords the desired compound in high purity and satisfactory yields. This invention provides a commercially viable one-step process for making such pyridylamino-pyrido[2,3-d]pyrimidines in high yield and high purity.

SUMMARY OF THE INVENTION

This invention provides a one-step chemical process for preparing 2-(pyridin-4-ylamino)-pyrido[2,3-d]pyrimidines comprising reacting a 4-aminopyridine with an alkali metal amide or hydride and a 2-alkylsulfanyl-6-aryl-8-substituted-8H-pyrido[2,3-d]pyrimidin-7-one. More particularly, the invention provides a process for reacting a 4-aminopyridine of the formula

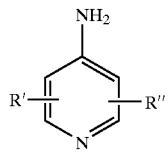

with an alkylsulfanyl compound of the Formula I

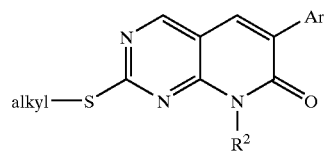

in the presence of an alkali metal hydride or amide to provide a compound of Formula II

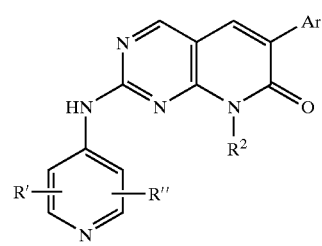

wherein:
"Alkyl" is $C_1$–$C_6$ alkyl;
R' and R" independently are hydrogen, $C_1$–$C_6$ alkyl, $C_1$–$C_6$ alkoxy, halo, hydroxy, phenyl, or $C_1$–$C_6$ alkanoyl;
$R^2$ is hydrogen, $(CH_2)_n$Ph, where Ph is phenyl or substituted phenyl, and n is 0, 1, 2, or 3; heteroaromatic, cycloalkyl, $C_1$–$C_6$ alkanoyl, $C_1$–$C_6$ alkyl, $C_2$–$C_6$ alkenyl, and $C_2$–$C_6$ alkynyl, where the alkyl, alkenyl, and alkynyl groups may be substituted by $NR_5R_6$, phenyl, substituted phenyl, thioalkyl, alkoxy, hydroxy, carboxy, halogen, cycloalkyl, and where $R_5$ and $R_6$ are independently hydrogen, $C_1$–$C_6$ alkyl, $C_2$–$C_6$ alkenyl, $C_2$–$C_6$ alkynyl, $(CH_2)_n$Ph where Ph is phenyl or substituted phenyl, and n is 0, 1, 2, or 3; cycloalkyl, heteroaromatic, and $R_5$ and $R_6$ taken together with the nitrogen to which they are attached can complete a ring having 3 to 7 carbon atoms and optionally containing 1, 2, or 3 heteroatoms selected from nitrogen, substituted nitrogen, oxygen, and sulfur;
Ar is phenyl, substituted phenyl, or heteroaromatic;
and the pharmaceutically acceptable salts thereof.
Preferably, R' and R" independently are hydrogen, $C_1$–$C_6$ alkyl, halogen, or phenyl; and
$R^2$ is hydrogen, $(CH_2)_n$Ph, where Ph is phenyl or substituted phenyl, and n is 0, 1, 2, or 3; heteroaromatic, cycloalkyl, $C_1$–$C_6$ alkyl, and $C_2$–$C_6$ alkenyl, where the alkyl and alkenyl groups may be substituted by $NR_5R_6$, phenyl, substituted phenyl, alkoxy, halogen, cycloalkyl, and where $R_5$ and $R_6$ are independently hydrogen, $C_1$–$C_6$ alkyl, $C_2$–$C_6$ alkenyl, $(CH_2)_n$Ph where Ph is phenyl or substituted phenyl, and n is 0, 1, 2, or 3; cycloalkyl, heteroaromatic, and $R_5$ and $R_6$ taken together with the nitrogen to which they are attached can complete a ring having 3 to 7 carbon atoms and optionally containing 1, 2, or 3 heteroatoms selected from nitrogen, substituted nitrogen, oxygen, and sulfur.

In a preferred embodiment, R' and R" both are hydrogen.
In another preferred embodiment, Ar is substituted phenyl and is more preferably 3,5-di-$C_1$–$C_6$ alkoxyphenyl. Ar is most preferably 3,5-dimethoxyphenyl.
In another preferred embodiment, $R^2$ is $C_1$–$C_6$ alkyl.
Preferably, halogen is bromo, chloro, or iodo.
In a further embodiment, the alkali metal hydride or amide is selected from the group consisting of lithium hydride, sodium hydride, lithium amide, and sodium amide.

DETAILED DESCRIPTION OF THE INVENTION

For purposes of the present invention, the terms "alkyl" and "$C_1$–$C_6$ alkyl" mean a straight or branched hydrocarbon radical having from 1 to 6 carbon atoms and include, for example, methyl, ethyl, n-propyl, isopropyl, n-butyl, sec-butyl, isobutyl, tert-butyl, n-pentyl, n-hexyl, and the like. The term "$C_1$–$C_6$ alkyl" includes within its definition the term "$C_1$–$C_3$ alkyl".

"Halo" or "halogen" includes fluoro, chloro, bromo, and iodo.

The terms "alkenyl" and "$C_2$–$C_6$ alkenyl" mean a straight or branched hydrocarbon radical having from 2 to 6 carbon atoms and 1 double bond and includes ethenyl, 3-buten-1-yl, 2-ethenylbutyl, 3-hexen-1-yl, and the like.

The terms "alkynyl" and "$C_2$–$C_6$ alkynyl" mean a straight or branched hydrocarbon radical having from 2 to 6 carbon atoms and at least one triple bond. Typical $C_2$–$C_6$ alkynyl groups include propynyl, 2-butyn-1-yl, 3-pentyn-1-yl, and the like.

The terms "cycloalkyl" and "$C_3$–$C_6$ cycloalkyl" mean a cyclic hydrocarbyl group such as cyclopropyl, cyclobutyl, cyclohexyl, and cyclopentyl.

The terms "alkoxy" and "$C_1$–$C_6$ alkoxy" refer to the alkyl groups mentioned above binded through oxygen, examples of which include methoxy, ethoxy, isopropoxy, tert-butoxy, and the like.

The term "$C_1$–$C_6$ alkanoyl" refers to an alkyl group, as defined above, linked through a carbonyl, i.e.,

Such groups include formyl, acetyl, propionyl, butyryl, and isobutyryl.

"Acyl" means an alkyl or aryl (Ar) group bonded through a carbonyl group

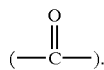

For example, acyl includes a $C_1$–$C_6$ alkanoyl, including substituted alkanoyl, wherein the alkyl portion can be substituted by $NR_5R_6$ or a carboxylic or heterocyclic group. Typical acyl groups include acetyl, benzoyl, and the like.

The alkyl, alkenyl, alkoxy, and alkynyl groups described above may be substituted. The substituent groups which may be part of the alkyl, alkenyl, alkoxy, and alkynyl groups are $NR_5R_6$, phenyl, substituted phenyl, thio($C_1$–$C_6$)alkyl, $C_1$–$C_6$ alkoxy, hydroxy, carboxy, $C_1$–$C_6$ alkoxycarbonyl, halo, cycloalkyl, and a 5- or 7-membered carbocyclic ring or heterocyclic ring having 1 or 2 heteroatoms selected from nitrogen, substituted nitrogen, oxygen, and sulfur. "Substituted nitrogen" means nitrogen bearing $C_1$–$C_6$ alkyl or $(CH_2)_n$Ph.

Examples of substituted alkyl groups thus include 2-aminoethyl, 2-diethylaminoethyl, 2-dimethylaminopropyl, ethoxycarbonylmethyl, 3-phenylbutyl, methylsulfanylmethyl, methoxymethyl, 3-hydroxypentyl, 2-carboxybutyl, 4-chlorobutyl, 3-cyclopropylpropyl, 3-morpholinopropyl, piperazinylmethyl, and 2-(4-methylpiperazinyl)ethyl.

Examples of substituted alkenyl groups thus include 2-diethylaminoethenyl, 3-amino-2-butenyl, 3-(1-piperazinyl)-1-propenyl, 3-hydroxy-1-propenyl, 2-(1-s-triazinyl)ethenyl, 3-phenyl-3-pentenyl, and the like.

Examples of substituted alkynyl groups include 2-methoxyethynyl, 2-ethylsulfanyethynyl, 4-(1-piperazinyl)-3-(butynyl), 3-phenyl-5-hexynyl, 3-diethylamino-3-butynyl, 4-chloro-3-butynyl, 4-cyclobutyl-4-hexynyl, and the like.

Typical substituted alkoxy groups include aminomethoxy, trifluoromethoxy, 2-diethylaminoethoxy, 2-ethoxycarbonylethoxy, 3-hydroxypropoxy, 6-carboxyhexyloxy, and the like.

Further, examples of substituted alkyl, alkenyl, and alkynyl groups include dimethylaminomethyl, carboxymethyl, 4-diethylamino-3-buten-1-yl, 5-ethylmethylamino-3-pentyn-1-yl, 4-morpholinobutyl, 4-tetrahydropyridinylbutyl-3-imidazolidin-1-ylpropyl, 4-tetrahydrothiazol-3-yl-butyl, phenylmethyl, 3-chlorophenylmethyl, and the like.

The term "Ar" refers to unsubstituted and substituted aromatic and heteroaromatic groups. Heteroaromatic groups have from 4 to 9 ring atoms, from 1 to 4 of which are selected from O, S, and N. Preferred groups have 1 or 2 heteroatoms in a 5- or 6-membered aromatic ring. Mono and bicyclic ring systems are included. Typical Ar groups include phenyl, 3,5-dimethoxyphenyl, 3-chlorophenyl, 2,6-dibromophenyl, pyridyl, 3-methylpyridyl, benzothienyl, 2,4,6-tribromophenyl, 4-ethylbenzothienyl, furanyl, 3,4-diethylfuranyl, naphthyl, 4,7-dichloronaphthyl, and the like.

Preferred Ar groups are phenyl and phenyl substituted by 1, 2, or 3 groups independently selected from halo, alkyl alkoxy, thio, thioalkyl, hydroxy, alkanoyl, —CN, —$NO_2$, —$COOR_8$, —$CF_3$, alkanoyloxy, or amino of the formula —$NR_5R_6$. The alkyl and alkoxy groups can be substituted as defined above. For example, typical groups are carboxyalkyl, i.e.,

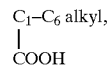

alkoxycarbonylalkyl

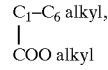

hydroxyalkyl and hydroxyalkoxy,

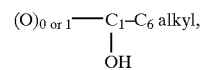

and alkoxyalkyl, i.e.,

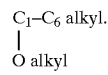

Disubstituted phenyl is most preferred, and 2,6-disubstituted phenyl and 3,5-disubstituted phenyl are especially preferred.

Typical Ar substituted phenyl groups which are preferred thus include 2-aminophenyl, 3-chloro-4-methoxyphenyl, 2,6-dimethylphenyl, 2,6-diethylphenyl, 3-hydroxyphenyl, 4-hydroxymethylphenyl, 3,4-dimethoxyphenyl, 3,5-dimethoxyphenyl, 2,6-dichlorophenyl, 4-(3-aminopropoxy) phenyl-, 2-chloro-6-methylphenyl, 2,4,6-trichlorophenyl, 2,6-dimethoxyphenyl, 4-(diethylaminoethoxy)phenyl, 2,6-dihydroxyphenyl, 2,6-dibromophenyl, 2,6-dinitrophenyl, 2,6-di-(trifluoromethyl)phenyl, 3-(dimethylaminoethyl) phenyl, 2,6-dimethylphenyl, 2,3,6-trimethylphenyl, 2,6-dibromo-4-methylphenyl, and the like.

The process of this invention is carried out by reacting the 2-(alkylsulfanyl)-pyrido[2,3-d]pyrimidine of Formula I, an alkali metal amide or hydride, with a 4-aminopyridine reagent in an organic solvent to provide the corresponding 2-(pyridin-4-yl-amino)-pyrido[2,3-d]pyrimidine of Formula II. The reaction occurs as shown below:

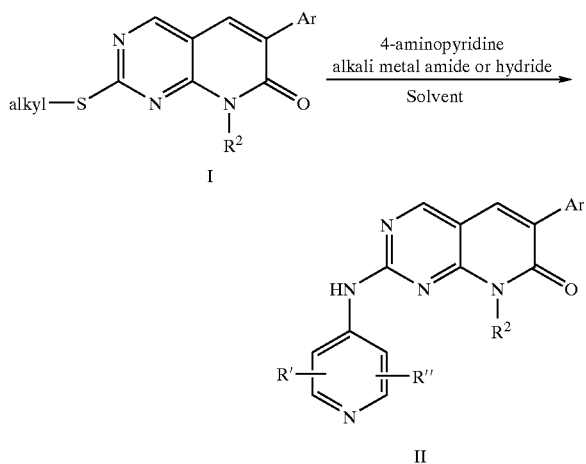

The 4-aminopyridine used in the process has the formula

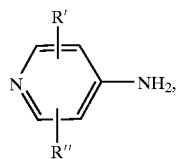

wherein R' and R" are the same substituents on the pyridyl ring portion of the finished product. The starting pyridopyrimidine of Formula I and the 4-aminopyridine typically are used in approximately equimolar amounts, whereas the alkali metal hydride or amide generally is used in an excessive amount, for example from about 2 to about 4 equivalents relative to the pyridopyrimidine starting material.

"Base" as used herein means the alkali metal hydride or amide. Typical bases include sodium hydride, sodium amide, lithium hydride, and lithium amide. Also included are potassium amide, potassium hydride, cesium amide and cesium hydride. A preferred alkali metal is lithium and a preferred base is lithium hydride.

The process of this invention is generally carried out in an unreactive organic solvent. The particular solvent is not critical. Typical solvents commonly used include dimethylsulfoxide, dimethylformamide, acetonitrile, tetrahydrofuran, glyme, diglyme, sulfolane, and N-methylpyrrolidinone (NMP). A nonpolar solvent such as tetrahydrofuran is preferred.

The reaction generally is substantially complete within about 1 hour to about 24 hours when carried out at a temperature of about 30° C. to about 120° C. While the exact temperature at which the reaction is conducted is not critical, heating above room temperature is generally preferred in order to promote substantially complete conversion within the above noted time ranges.

The final product of the process, a 2-(pyridin-4-ylamino)-pyridopyrimidine compound of Formula II, is readily isolated by simply adding water to the reaction mixture to quench the process and to destroy any remaining alkali metal hydride or amide, and then filtering the reaction mixture and, if desired, washing the precipitate with a solvent such as water or an organic solvent such as acetonitrile or methanol. The solid product generally is dried in a vacuum oven at about 30° C. to about 50° C.

If desired, the product of Formula II can be further purified by routine processes such as chromatography, recrystallization from solvents such as DMSO, or it can be converted to a pharmaceutically acceptable acid addition salt.

Pharmaceutically acceptable acid addition salts of the compound of Formula II include salts derived from inorganic acids such as hydrochloric, nitric, phosphoric, sulfuric, hydrobromic, hydriodic, phosphorous, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M., et al., "Pharmaceutical Salts," *J. of Pharmaceutical Science,* 1977;66:1–19).

The acid addition salts of the basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise, the salts are equivalent to their respective free base for purposes of the present invention.

The starting material required for the present process is a 2-(alkylsulfanyl)-pyrido[2,3-d]pyrimidine of Formula I. The 2-alkylsulfanyl compound is available as described in U.S. Pat. No. 5,733,914. For example, an arylacetonitrile is condensed with a 2-alkylsulfanyl-4-substituted aminopyrimidin-5-carboxaldehyde in the presence of a mild base to give a 2-(alkylsulfanyl)-6-aryl-8-substituted-8H-pyrido[2,3-d]pyrimidine-7-imine. The 7-imino group is readily oxidized by reaction with an acid to give the 2-(alkylsulfanyl)-pyridopyrimidine-7-one of Formula I.

A preferred method for preparing the 2-(alkylsulfanyl) compounds of Formula I comprises reacting the 2-(alkylsulfanyl)-4-substituted amino-pyrimidin-5-carboxaldehyde with an aryl acetic acid ester instead of an aryl acetonitrile. Use of the aryl acetic acid ester provides the pyridopyrimidine-7-one directly in high yield.

The present one-step process provides pyridin-4-yl pyridopyrimidines in high yield and excellent purity. The following detailed examples further illustrate the process of this invention. The examples are provided as illustration only, and are not intended to limit the invention in any respect.

PREPARATION 1

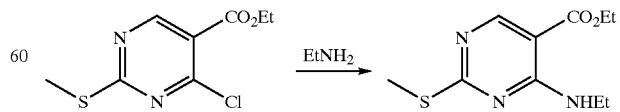

4-Ethylamino-2-Methysulfanyl-Pyrimidine-5-Carboxylic Acid Ethyl Ester

A 22-L, 4-necked round-bottomed flask was equipped with a mechanical stirrer, a dropping funnel, and a thermometer. The flask was charged with the ethyl 4-chloro-2-(methylthio)-5-pyrimidinecarboxylate (1.53 kg, 6.56 mol), triethylamine (2.74 L, 19.7 mol, 3 eq), and 7.5 L of tetrahydrofuran to give a solution. The aqueous ethylamine (0.53 L, 6.56 mol, 1 eq) was added via the dropping funnel over 20 minutes. The reaction temperature rose to 35° C. during the addition. The reaction was stirred at ambient temperature for 2 hours. The reaction was checked for completion using TLC (SiO$_2$; 7:3/heptane:ethyl acetate). The precipitate (triethylamine hydrochloride) was filtered off and washed 2 times with tetrahydrofuran, combining the washes with the original filtrate. The tetrahydrofuran was stripped to near dryness on a rotary evaporator. The residue was partitioned between saturated aqueous sodium bicarbonate (500 mL) and ethyl acetate (1 L). Note that there is carbon dioxide gas evolution from the bicarbonate both during the partitioning and the subsequent washes. The layers were separated and the organic layer washed 2 times with saturated aqueous sodium bicarbonate and 1 time with brine. The solution was dried over magnesium sulfate, filtered, and stripped to give the titled compound as an off-white solid. Yield: 95%.

PREPARATION 2

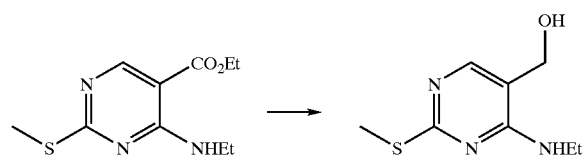

4-Ethylamino-2-methylsulfanyl-pyrimidin-5-yl)-methanol

The 50-L built-in reactor was purged with argon 3 times, and then a positive argon pressure was maintained throughout the process. The reactor was charged with 4 L of tetrahydrofuran, followed by lithium aluminum hydride (1 M in tetrahydrofuran, 6.77 kg, 7.48 L, 7.48 mol, 1.2 eq). The chiller/heater was set to 18° C. and activated. The product of Preparation 1,4-ethylamino-2-methylsulfanyl-pyrimidine-5-carboxylic acid ethyl ester (1.5 kg, 6.23 mol, 1 eq), was dissolved in 11 L of tetrahydrofuran (0.58 M) and was added to the reaction vessel using a pump over ~2 hours. TLC (SiO$_2$; 7:3/heptane:ethyl acetate) was used to monitor the reaction for completion. When the reaction was complete, the chiller/heater was set to 10° C. The excess hydride was quenched by adding successively: 1.25 L of water, 1.25 L of 15 wt % sodium hydroxide, and then 4.1 L of water. The first portion of water was added quite slowly and with vigorous stirring to keep down the foaming and to keep the temperature below 30° C. As the quench continues, the addition rate was gradually increased until the final portion of water could be added in a steady stream. The reaction mixture was then stirred for 1 hour before filtering through a 1-inch plug of celite in a 2 L coarse fritted funnel. The salts were washed once with tetrahydrofuran on the funnel. The tetrahydrofuran was stripped, then the residue azeotroped 2 times with 1 L portions of toluene. The resulting solid was washed from the flask using heptane, then dried in a vacuum oven at 40° C. to give the titled compound which is used in the next step without further purification.

PREPARATION 3

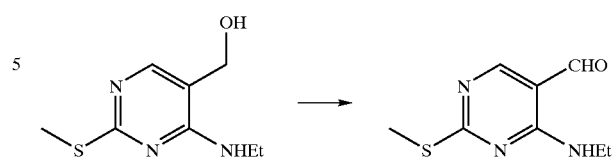

4-Ethylamino-2-methylsulfanyl-pyrimidine-5-carboxaldehyde

A 50-L round-bottomed flask equipped with a mechanical stirrer was charged with 565 g (2.84 mol) of the product of Preparation 2,4-ethylamino-2-methylsulfanyl-pyrimidin-5-yl)-methanol 1.23 kg (14.2 mol, 5 eq) of manganese (IV) oxide, and 19 L of chloroform. The mixture was stirred 24 hours at room temperature, then checked by TLC (SiO$_2$; 7:3/heptane:ethyl acetate) for completion of reaction. The reaction was filtered through a plug of celite and the chloroform stripped to give the titled compound in 90% yield.

EXAMPLE 1

2-(Methylsulfanyl)-6-(3,5-dimethoxyphenyl)-8-ethyl-8H-pyrido[2,3-d]-pyrimidine-7-one

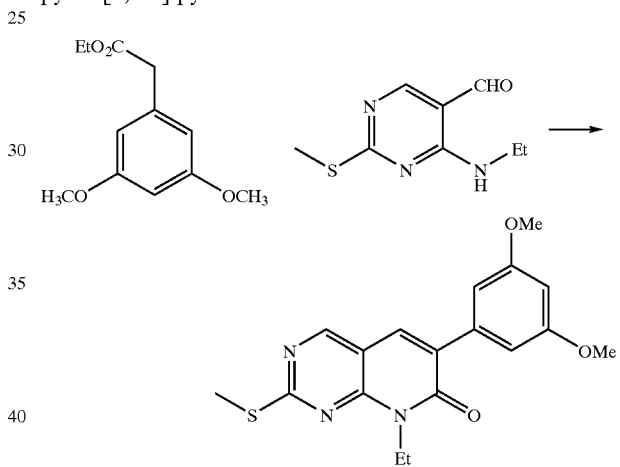

A 5-L round bottomed flask was charged with 516 g (2.62 mol) of 4-ethylamino-2-methylsulfanyl-pyrimidine-5-carboxaldehyde, 587 g (2.62 mol) of (3,5-dimethoxyphenyl)-acetic acid ethyl ester and 391 mL (2.62 mol) of 1,8-diazabicyclo[5.4.0]undec-7-ene. The mixture was heated at 80° C. for 1 hour. Thin layer chromatography (TLC) (silica, 6:4/heptane:ethyl acetate, developed in an iodine chamber) showed all the 4-ethylamino-2-methylsulfanyl-pyrimidine-5-carbaldehyde was consumed. Ethyl alcohol (absolute, 2.75 L) was added to the reaction vessel, which was allowed to cool to room temperature. The solid was collected by filtration, washed once with ethyl alcohol, and dried in a vacuum oven at 45° C. for 12 hours to provide 530 g (57% yield) of 2-(methylsulfanyl)-6-(3,5-dimethoxyphenyl)-8-ethyl-8H-pyrido[2,3-d]pyrimidin-7-one. Proton NMR (s,1H), 6.83 (d, 2H), 6.51 (s, 1H), 4.36 (q, 2H), 3.75 (s, 1H), 2.58 (s, 3H), (t, 3H). The combined mother liquor and washes were allowed to stand at room temperature for 7 days. At this time a second crop was collected, washed once with ethyl alcohol, and dried in a vacuum oven at 45° C. for 12 hours to provide 79 g (8.5% yield) of 2-(methylsulfanyl)-6-(3,5-dimethoxyphenyl)-8-ethyl-8H-pyrido[2,3-d]pyrimidine-7-one. Proton NMR (DMSO) is consistent with the structure.

EXAMPLE 1A 2-(Methylsulfanyl)-6-(3,5-dimethoxyphenyl)-8-ethyl-8H-pyrido[2,3-d]-pyrimidine-7-one 4.8 Kg of 4-ethylamino-2-methylsulfanyl-pyrimidine-5-carboxaldehyde and 5.5 Kg of (3,5-dimethoxyphenyl)-acetic acid ethyl ester were dissolved in 10 L of DMSO at room temperature and stirred. 4.4 Kg of 1,8-diazabicyclo[5.4.0] undec-7-ene was added to the reaction mixture. The mixture was heated at about 45–50° C. for at least 3 hours. The reaction was monitored by reverse-phase HPLC. When the reaction was completed, ethyl alcohol (3 L) was added to the reaction vessel, which was cooled to 5–15° C. The yellow product was precipitated and collected by filtration, washed with a mixture of isopropyl alcohol and water (3 L+3 L), and dried in a vacuum tray dryer at about 40–45° C. for at least 12 hours using a house vacuum (~30 in Hg) to provide 7.3 Kg (84% yield) of 2-(methylsulfanyl)-6-(3,5-dimethoxyphenyl)-8-ethyl-8H-pyrido[2,3-d]pyrimidine-7-one. Proton NMR is consistent with the structure.

EXAMPLE 2

2-(Pyridin-4-ylamino)-6-(3,5-dimethoxyphenyl)-8-ethyl-8H-pyrido[2,3-d]-pyrimidin-7-one To a 100-mL, three-neck, round bottom flask were added 294.0 mg (3.124 mM) of 4-aminopyridine, 238.8 mg (10.40 mM) of lithium amide, and 15 mL of tetrahydrofuran. The reaction mixture was heated to 50° C. for 1 hour. A solution of 998 mg (2.792 mM) of 2-(methylsulfanyl)-6-(3,5-dimethoxyphenyl)-8-ethyl-8H-pyrido[2,3-d]pyrimidin-7-one in 25 mL of tetrahydrofuran was added in one portion. The reaction mixture was heated at reflux for 24 hours. The reaction mixture was cooled to 50° C. and diluted by dropwise addition of 25 mL of water. The solid precipitate was collected by filtration and dried in a vacuum oven at 45° C. for 12 hours to provide 93.6% yield of the filtered compound, mp 305–307° C. Mass Spec (APCI) 403.9 m/z. HPLC established the product was 98.5% pure.

EXAMPLE 3

2-(Pyridin-4-ylamino)-6-(3,5-dimethoxyphenyl)-8-ethyl-8H-pyrido[2,3-d]-pyrimidin-7-one hydrochloride To a solution of 88 g (0.93 mol) of 4-aminopyridine in 1 L of tetrahydrofuran was added 21.2 g (2.67 mol) of lithium hydride. The reaction mixture was heated to 50° C. for 1 hour. To the stirred reaction mixture was added a solution of 318 g (0.89 mol) of 2-(methylsulfanyl)-6-(3,5-dimethoxyphenyl)-8-ethyl-8H-pyrido[2,3-d]pyrimidin-7-one in 1.8 L of tetrahydrofuran. The reaction solution was heated at reflux for 24 hours, and then cooled to 50° C. The reaction mixture was diluted by the slow addition of a mixture of 500 mL of water and 1 L of 6N hydrochloric acid. The reaction mixture was cooled to 24° C. and stirred for 16 hours. The reaction mixture was further diluted by addition of 250 mL of acetonitrile and 200 mL of water, and stirring was continued for an additional 2 hours. The mixture was then filtered, and the filter cake was dried at 45° C. in vacuo for 12 hours to provide 360 g (92%) of 2-(pyridin-4-ylamino)-6-(3,5-dimethoxyphenyl)-8-ethyl-8H-pyrido[2,3-d]pyrimidin-7-one hydrochloride, mp 295–300° C. (dec). HPLC established the purity at 98%. Mass Spec (APCI) 439.89 m/z.

EXAMPLE 4

Following the general procedure of Examples 2 and 3, 791.0 mg (8.404 mM) of 4-aminopyridine was reacted with 212.5 mg (26.73 mM) of lithium hydride and 3002.4 mg (8.4 mM) of 2-(methylsulfanyl)-6-(3,5-dimethoxyphenyl)-8-ethyl-8H-pyrido[2,3-d]pyrimidin-7-one to give 92.7% yield (95.9% purity) of 2-(pyridin-4-ylamino)-6-(3,5-dimethoxyphenyl)-8-ethyl-8H-pyrido[2,3-d]pyrimidin-7-one.

EXAMPLE 5

By following the general procedure of Examples 2 and 3, 524.2 mg (5.569 mM) of 4-aminopyridine was reacted with 687.4 mg (17.2 mM) of sodium hydride and 1983.8 mg (5.550 mM) of 2-(methylsulfanyl)-6-(3,5-dimethoxyphenyl)-8-ethyl-8H-pyrido[2,3-d]pyrimidin-7-one to provide 66.3% yield (85.8% purity) of 2-(pyridin-4-ylamino)-6-(3,5-dimethoxyphenyl)-8-ethyl-8H-pyrido[2,3-d]pyrimidin-7-one.

What is claimed is:

1. A process for preparing a 2-(pyridin-4-ylamino)-pyrido[2,3-d]pyrimidine of Formula II

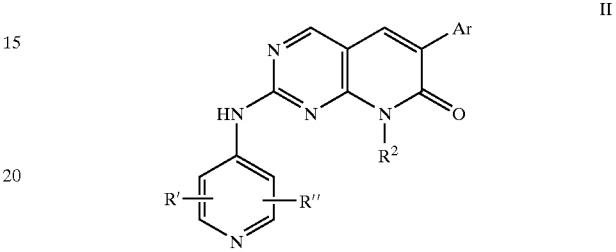

comprising reacting a 4-aminopyridine of the formula

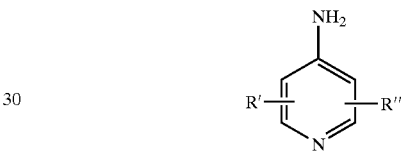

with an alkali metal amide or hydride and a 2-alkylsulfanyl-pyrido[2,3-d]pyrimidine of Formula I

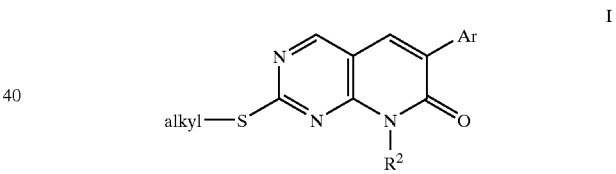

wherein:

R' and R" independently are hydrogen, $C_1$–$C_6$ alkyl, halogen, or phenyl;

$R^2$ is hydrogen, $(CH_2)_n$Ph, where Ph is phenyl or substituted phenyl, and n is 0, 1, 2, or 3, heteroaromatic, cycloalkyl, $C_1$–$C_6$ alkyl, and $C_2$–$C_6$ alkenyl, where the alkyl and alkenyl groups may be substituted by $NR_5R_6$, phenyl, substituted phenyl, alkoxy, halogen, cycloalkyl;

$R_5$ and $R_6$ are independently hydrogen, $C_1$–$C_6$ alkyl, $C_2$–$C_6$ alkenyl, $(CH_2)_n$Ph where Ph is phenyl or substituted phenyl, and n is 0, 1, 2, or 3, cycloalkyl, heteroaromatic, $R_5$ and $R_6$ taken together with the nitrogen to which they are attached can complete a ring having 3 to 7 carbon atoms and optionally containing 1, 2, or 3 heteroatoms selected from nitrogen, substituted nitrogen, oxygen, and sulfur; and Ar is phenyl, substituted phenyl, or heteroaromatic.

2. A process according to claim 1 wherein Ar is substituted phenyl.

3. A process according to claim 1 wherein Ar is di-$C_1$–$C_6$ alkoxy phenyl.

4. A process according to claim 1 wherein $R^2$ is $C_1$–$C_6$ alkyl.

5. A process according to claim 1 wherein R' and R" both are hydrogen.

6. A process for preparing a compound of the formula

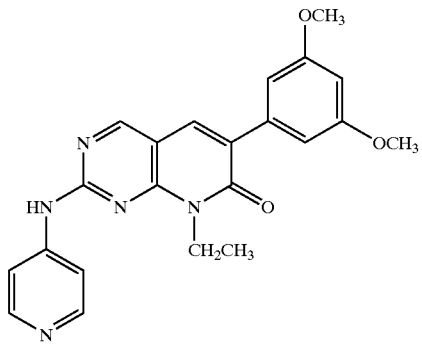

comprising reacting 4-aminopyridine with a compound of the formula

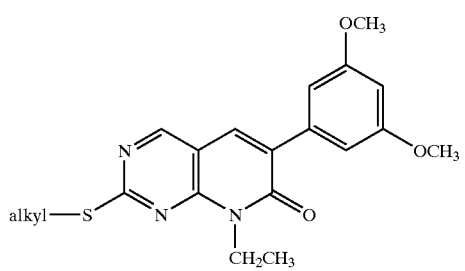

in the presence of a base selected from the group consisting of lithium amide, sodium amide, lithium hydride, and sodium hydride.

* * * * *